US009642562B2

(12) United States Patent
Stout (10) Patent No.: US 9,642,562 B2
(45) Date of Patent: May 9, 2017

(54) BIO-SURVEILLANCE SYSTEM (75) Inventor: Todd Stout, Rancho Santa Fe, CA (US)

(73) Assignee: Stout Solutions, LLC, Encinitas, CA (US)

( * ) Notice: Subject to any disclaimer, the term of this patent is extended or adjusted under 35 U.S.C. 154(b) by 25 days.

(21) Appl. No.: 10/524,918

(22) PCT Filed: Aug. 19, 2003

(86) PCT No.: PCT/US03/25967
§ 371 (c)(1),
(2), (4) Date: Jul. 5, 2005

(87) PCT Pub. No.: WO2004/030512
PCT Pub. Date: Apr. 15, 2004

(65) Prior Publication Data
US 2006/0152372 A1    Jul. 13, 2006

Related U.S. Application Data

(60) Provisional application No. 60/404,364, filed on Aug. 19, 2002.

(51) Int. Cl.
*A61B 5/00* (2006.01)
*A61B 5/11* (2006.01)
(Continued)

(52) U.S. Cl.
CPC .......... *A61B 5/1112* (2013.01); *A61B 5/0002* (2013.01); *G06F 19/3493* (2013.01); *G08B 21/10* (2013.01); *G08B 31/00* (2013.01)

(58) Field of Classification Search
USPC ......... 600/300–301; 128/920–925, 898–899; 705/2–4; 702/19
See application file for complete search history.

(56) References Cited

U.S. PATENT DOCUMENTS 5,860,918 A * 1/1999 Schradi et al. ............... 600/300
6,010,451 A   1/2000 Clawson
(Continued)

OTHER PUBLICATIONS

Goldenberg et al. "Early statistical detection of anthrax outbreaks by tracking over-the-counter medication sales" Proceedings of the National Academy of Sciences of the United States of America.*
(Continued)

*Primary Examiner* — William Thomson
*Assistant Examiner* — Bobby Soriano
(74) *Attorney, Agent, or Firm* — Carlson, Gaskey & Olds, P.C.

(57) ABSTRACT

A bio-surveillance system monitors symptoms or groups of symptoms experienced by people in a geographical area. The system tracks symptoms reported by calls to an emergency service dispatcher. The bio-surveillance system monitors the symptoms and associates the geographical location with the symptoms. Various triggers are programmed and stored in the system to look for certain types of threats. Each trigger is set based on a statistical variation of the historical data relating to the symptoms within a predetermined time in a predefined geographical area. When the reported symptoms exceed one of the triggers, an alert is activated to provide an indication of a potential biological or chemical terrorist attack.

21 Claims, 10 Drawing Sheets

(51) Int. Cl.
*G06F 19/00* (2011.01)
*G08B 21/10* (2006.01)
*G08B 31/00* (2006.01)

(56) References Cited

U.S. PATENT DOCUMENTS

| | | | |
|---|---|---|---|
| 6,139,494 A | 10/2000 | Cairnes | |
| 6,231,519 B1* | 5/2001 | Blants et al. | 600/300 |
| 6,398,728 B1* | 6/2002 | Bardy | A61B 5/0031 |
| | | | 128/920 |
| 6,527,712 B1* | 3/2003 | Brown | G06F 19/3493 |
| | | | 128/923 |
| 7,024,370 B2* | 4/2006 | Epler et al. | 705/3 |
| 2003/0009239 A1* | 1/2003 | Lombardo | G06F 19/3493 |
| | | | 700/30 |
| 2003/0023416 A1* | 1/2003 | Peterson | G06F 19/3493 |
| | | | 703/2 |
| 2003/0065409 A1* | 4/2003 | Raeth | G05B 9/02 |
| | | | 700/31 |
| 2003/0129578 A1* | 7/2003 | Mault | G01N 33/50 |
| | | | 435/4 |
| 2003/0187809 A1* | 10/2003 | Suermondt | G06F 19/3493 |
| | | | 706/46 |
| 2004/0116821 A1* | 6/2004 | Beiswenger | G06F 19/3493 |
| | | | 600/549 |
| 2010/0138160 A1* | 6/2010 | Jacquez | G06F 19/3437 |
| | | | 702/19 |

OTHER PUBLICATIONS

U.S. Department of Health and Human Services, Centers for Disease Control and Prevention, The Public Health Response to Biological and Chemical Terrorism, Interim Planning Guidance for State Public Health Officials, Jul. 2001 http://www.bt.cdc.gov/Documents/Planning/PlanningGuidance.PDF.*

* cited by examiner

Trigger Alert Call Information

| | | | Start Date/Time: 1/30/02 6:35:47 PM | End Date/Time: 1/31/02 6:35:47 AM |
|---|---|---|---|---|
| | | | Priorities: 1, 2, & 3 Only | Problems: Trigger Only |
| | | | Excludes Responses Where No Vehicle Arrived At Scene | |

| Time Sent To Queue | Pri | Problem | Response # | Unit | Address/Location | Trans |
|---|---|---|---|---|---|---|
| 1/30/02 7:02:11 PM | 2 | Unknown Problem (Man Dow | 0201300323 | 141 | 1339 75th Ter E, KCMo, MO | 0 |
| 1/30/02 7:13:38 PM | 2 | Unknown Problem (Man Dow | 0201300328 | 142 | 17205 Cherry, KCMo | 0 |
| 1/30/02 7:30:28 PM | 2 | Sick Person | 0201300334 | 119 | 2908 98th Ter E, KCMo, MO | 0 |
| 1/30/02 7:34:28 PM | 2 | Sick Person | 0201300345 | 163 | 3817 Maddi Ave, KCMo, MO | 1 |
| 1/30/02 8:27:30 PM | 2 | Unknown Problem (Man Dow | 0201300353 | 312 | 5504 Crest Dr, KCKs, KS | 0 |
| 1/30/02 9:09:41 PM | 2 | Sick Person | 0201300368 | 244 | 1613 Lowell Ave, KCKs, KS | 0 |
| 1/30/02 9:24:26 PM | 2 | Sick Person | 0201300375 | 109 | 4637 Ne 112th St, KCMo, MO | 1 |
| 1/30/02 9:40:43 PM | 2 | Sick Person | 0201300384 | 115 | 301 Walnut St, KCMo, MO | 1 |
| 1/30/02 10:04:11 PM | 2 | Sick Person | 0201300390 | 225 | 3235 29th St N, KCKs, KS | 1 |
| 1/30/02 10:17:32 PM | 2 | Sick Person | 0201300393 | 142 | 4231 67th Ter E, KCMo, MO | 1 |
| 1/30/02 10:24:56 PM | 2 | Sick Person | 0201300396 | 244 | 83 13th St N, 81.5, KCKs, KS | 1 |
| 1/30/02 10:38:03 PM | 2 | Unknown Problem (Man Dow | 0201300401 | 104 | 4901 Brighton Ave N, 166, KCMo, MO | 0 |
| 1/30/02 10:43:58 PM | 2 | Sick Person | 0201300408 | AMR | 2913 Sterling Ave, KCMo, MO | 0 |
| 1/30/02 10:49:17 PM | 2 | Sick Person | 0201300410 | 163 | 10970 Wornall Rd, 761, KCMo, MO | 1 |
| 1/30/02 11:31:35 PM | 2 | Sick Person | 0201300422 | 107 | 3338 Euclid Ave, KCMo, MO | 0 |
| 1/30/02 11:37:49 PM | 2 | Unknown Problem (Man Dow | 0201300426 | 158 | 1354 10th St E, 7, KCMo, MO | 0 |
| 1/30/02 11:58:50 PM | 2 | Abdominal Pain/Problems | 0201300432 | 141 | 6951 Nw 70th St, KCMo, MO | 1 |
| 1/31/02 12:14:26 AM | 2 | Sick Person | 0201310003 | 107 | 3019 Ne Davidson Rd, KCMo, MO | 1 |
| 1/31/02 1:11:37 AM | 2 | Unknown Problem (Man Dow | 0201310015 | 130 | 3112 Brooklyn Ave, KCMo, MO | 0 |
| 1/31/02 2:26:49 AM | 2 | Abdominal Pain/Problems | 0201310030 | 113 | 414 6th St E, KCMo, MO | 1 |
| 1/31/02 2:38:03 AM | 2 | Sick Person | 0201310033 | 163 | 3581 Michigan Ave, KCMo, MO | 1 |
| 1/31/02 2:52:27 AM | 2 | Unknown Problem (Man Dow | 0201310038 | 135 | 2039 Paseo Blvd, KCMo, MO | 1 |
| 1/31/02 2:55:45 AM | 2 | Unknown Problem (Man Dow | 0201310039 | Car 16 | 3431 Paseo Blvd, KCMo, MO | 0 |
| 1/31/02 3:25:53 AM | 2 | Sick Person | 0201310045 | 244 | 522 Beech St, Edwardsville, KS | 1 |
| 1/31/02 3:33:07 AM | 2 | Sick Person | 0201310048 | 107 | 7440 9th St E, 2, KCMo, MO | 1 |
| 1/31/02 3:37:29 AM | 2 | Unknown Problem (Man Dow | 0201310049 | 208 | 4th St N.& Minnesota Ave, KCKs, KS | 0 |
| 1/31/02 3:38:45 AM | 2 | Unknown Problem (Man Dow | 0201310050 | 119 | 2609 Holmes St, KCMo, MO | 0 |
| 1/31/02 4:13:16 AM | 2 | CO/ Inhalation/ Haz Mat | 0201310056 | 113 | 8814 61st St E, KCMo, MO | 3 |
| 1/31/02 4:15:15 AM | 2 | Abdominal Pain/Problems | 0201310058 | 132 | 3111 Oak St, 1, KCMo, MO | 1 |
| 1/31/02 4:15:33 AM | 2 | CO/ Inhalation/ Haz Mat | 0201310057 | Car 16 | 3451 61st St E, KCMo, MO | 0 |
| 1/31/02 4:30:00 AM | 2 | CO/ Inhalation/ Haz Mat | 0201310063 | 119 | 7651 61st St E, KCMo, MO | 4 |
| 1/31/02 4:51:06 AM | 2 | Unknown Problem (Man Dow | 0201310065 | 135 | 159 34th St W, 293, KCMo, MO | 1 |
| 1/31/02 4:57:21 AM | 2 | Sick Person | 0201310069 | Car 16 | 3291 Blue Hills Rd, KCMo, MO | 0 |
| 1/31/02 4:58:09 AM | 2 | Sick Person | 0201310070 | 161 | 3291 Blue Hills Rd, KCMo, MO | 1 |

Total Responses: 34　　　　　　　　　　　　　　　　　　　　　　　　　　　　Total Transports: 24

BIO-SURVEILLANCE SYSTEM

REFERENCE TO RELATED APPLICATIONS

This application is a National Stage Application of PCT Application PCT/US03/025967 filed on Aug. 19, 2003, which claims priority to United States Patent Application 60/404,364 filed on Aug. 19, 2002.

BACKGROUND OF THE INVENTION

The present invention relates generally to a bio-surveillance system that monitors the symptoms of people in need of medical assistance and generates an alert when the monitored symptoms exceed a trigger.

Emergency services dispatchers use a dispatcher computer system that prompts them through a series of questions to ask a caller about the details of the emergency, such as the symptoms of a person needing medical assistance. Based upon the responses to the questions, the dispatcher computer system makes a preliminary assessment or diagnosis which is communicated to the emergency response personnel.

Recently, there have been fears of biological or chemical terrorist attacks. In response to these fears, the assignee of the present invention has developed a bio-surveillance system that monitors the number of occurrences of certain assessments or diagnosis from the dispatcher computer system. The bio-surveillance system compares a trailing 12-hour total of selected assessments to a trigger threshold, which varies based upon the time of the day and the day of the week. The trigger is set to some statistical variation of the historical data, such as the historical average plus two standard deviations. When the number of assessments exceeds the trigger, an alert is activated that indicates that there may possibly be a biological or chemical attack. The system assists emergency personnel and governmental authorities in identifying and responding to a potential threat as early as possible.

There are several drawbacks to the existing system. For one, the bio-surveillance system relies upon the preliminary assessment or diagnosis of the dispatchers. By following the pre-programmed series of questions, the dispatchers have a strong tendency to make assessments that are statistically more likely, and they are unlikely to make conclusions of statistically unlikely problems.

For example, although there is a current concern regarding biological attacks, a dispatcher is unable, or unlikely, to conclude based upon the responses to the questions that the person in need of assistance has Anthrax, small pox or is suffering from a chemical attack or other extremely rare problem. The dispatcher computer system is programmed to quickly assess statistically high likelihood problems and is not programmed to assess rare diseases from terrorist attacks.

The existing bio-surveillance system is also limited in its use of the triggers and its ability to change triggers. In the existing system, the system must be taken off-line to change a trigger, and the trigger must be rebuilt statistically based upon the historical data. For example, if the administrator of the system wants to increase the sensitivity of the system in response to current threats, such as by reducing the trigger from the historical average plus three standard deviations to the historical average plus two standard deviations, the system is taken off-line, and the trigger is rebuilt by reprocessing all of the historical data. Therefore, it is difficult to temporarily change the trigger quickly.

Further, in the existing system, calls and their associated assessments are indexed according to the address information, which can then be displayed in a listing of all the calls along with the problems to try to determine geographic relationships. However, it is difficult to determine geographic relationships simply based upon addresses and because different dispatchers may make different assessments.

SUMMARY OF THE INVENTION

The bio-surveillance system of the present invention alerts authorities of a potential biological or chemical terrorist attack or other event by monitoring symptoms reported to emergency services dispatchers. When a person is in need of medical assistance, a caller contacts an emergency service dispatcher. The emergency services dispatcher inputs the symptoms into a dispatcher computer system, and the symptom information is provided to a local central computer.

Various triggers are programmed and stored in the bio-surveillance system. Each trigger is set based on a statistical variation of the historical data of a symptom or a group of symptoms at various times of the day and days of the week. The local central computer monitors the symptoms or the groups of symptoms to look for certain types of threats. When the reported symptoms or groups of symptoms exceed one of the triggers, an alert is activated, indicating the possibility of a terrorist attack or other rare event. Various symptoms in a trigger can also be weighted.

The triggers of the bio-surveillance system can be changed "on the fly." Therefore, an administrator can quickly define and change a trigger to represent certain criteria without having to wait for a recalculation of the entire trigger. The reports symptoms can then be compared to the redefined trigger to detect a threat.

The data from the local central computer in a geographic region can be sent via a secure Internet connection to a main central computer which performs the analysis described above on a larger regional, state or national scale. The main central computer can have different triggers form the triggers used with the local central computer.

These and other features of the present invention will be best understood from the following specification and drawings.

BRIEF DESCRIPTION OF THE DRAWINGS

The various features and advantages of the invention will become apparent to those skilled in the art from the following detailed description of the currently preferred embodiment. The drawing that accompany the detailed description can be briefly described as follows:

FIG. 9 illustrates a report of reported symptoms, addresses and time of calls reported to a dispatcher center; and FIG. 10 schematically illustrates numerous local bio-surveillance systems which communicate with a main central computer.

DETAILED DESCRIPTION OF THE PREFERRED EMBODIMENT

Figure 1:
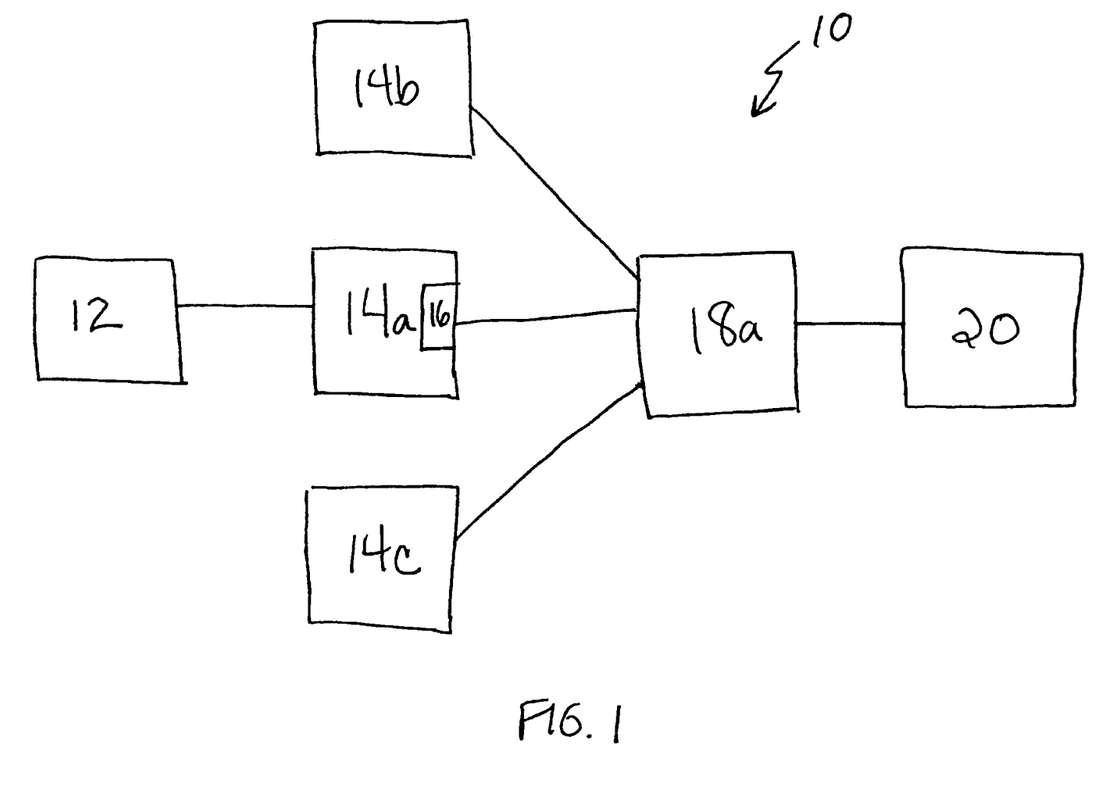
FIG. 1 schematically illustrates the bio-surveillance system of the present invention.
Figure 1D:
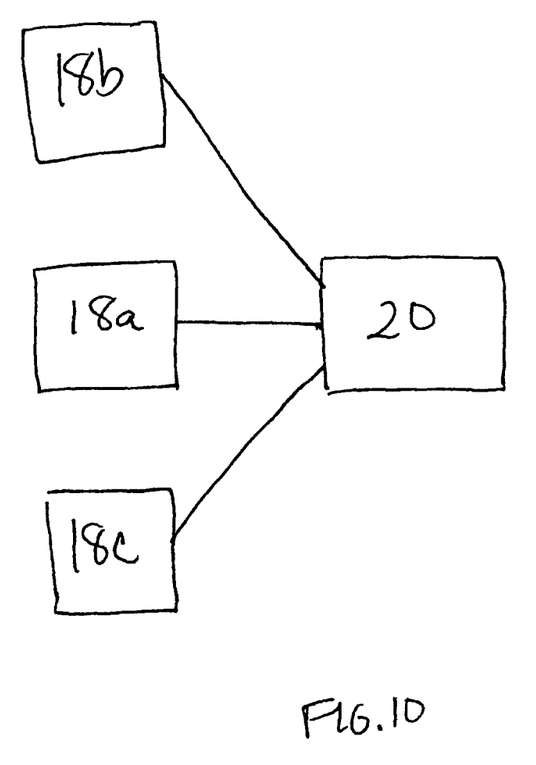

FIG. 1 schematically illustrates the bio-surveillance system 10 of the present invention. The bio-surveillance system 10 alerts authorities of a potential occurrence of an unusual or rare nature, such as a biological or chemical terrorist attack or other event. By statistically examining the symptoms described in calls compared to historical data and the geographic locations of the incidents, the bio-surveillance system 10 can quickly alert authorities that a biological or chemical terrorist attack or other rare event has possibly occurred. The bio-surveillance system 10 monitors the symptoms from all of the calls in a geographical area to provide a detection as early as possible.

When a person is in need of medical assistance, a caller contacts an emergency services dispatcher at a dispatcher center 14. Usually, the caller contacts the emergency service dispatcher by telephone 12, for example by calling 9-1-1. A dispatcher computer system 16 prompts the emergency services dispatcher to ask the caller about the symptoms the person in need of medical assistance is experiencing through a series of questions. The emergency services dispatcher inputs the responses to the questions and the symptoms into the dispatcher computer system 16. The dispatcher computer system 16 then provides this information to a local central computer 18a. Other local dispatch centers 14b and 14c also communicate with the local central computer 18a. The local dispatch centers 14a, 14b and 14c preferably communicate information to the local central computer 18a after each call.

Based upon a single call or even a few calls, an emergency services dispatcher is unlikely or unable to determine that a chemical or biological attack or other rare event has occurred. The bio-surveillance system 10 monitors the underlying responses to the questions, including the symptoms experienced by the person in need of medical assistance. For example, the symptoms can include headache, fever, fainting, clammy, unconscious, bleeding, vomiting, nausea, etc, or any other type of symptoms.

The dispatcher computer system 16 identifies the address of the caller and associates the address and the time of the call with the symptoms the person is experiencing. The dispatcher computer system 16 relays the address to the local central computer 18a. The address of the caller is geo-coded to a specific latitude and a longitude, and the local central computer 18a tracks the symptoms reported by the various calls placed to the local dispatch centers 14a, 14b and 14c.

Various triggers are programmed and stored in the bio-surveillance system 10 to look for certain types of threats. Each trigger is based on a statistical variation of historical data of the occurrence of the symptoms or various symptoms in a geographical area. Each trigger can vary based on the time of day and the day of the week. The triggers can be customized by an administrator to look for specific threats in a given geographical area.

When the symptoms reported by the local dispatch centers 14a, 14b and 14c exceed one of the triggers, an alert is activated. The alert can be transmitted by pager, email, an on-screen message, fax, a printed report, or any other method of alerting a user. The alert can also provide information of whether the alert is a serious event or if it simply an increase in non-related calls.

Figure 2:
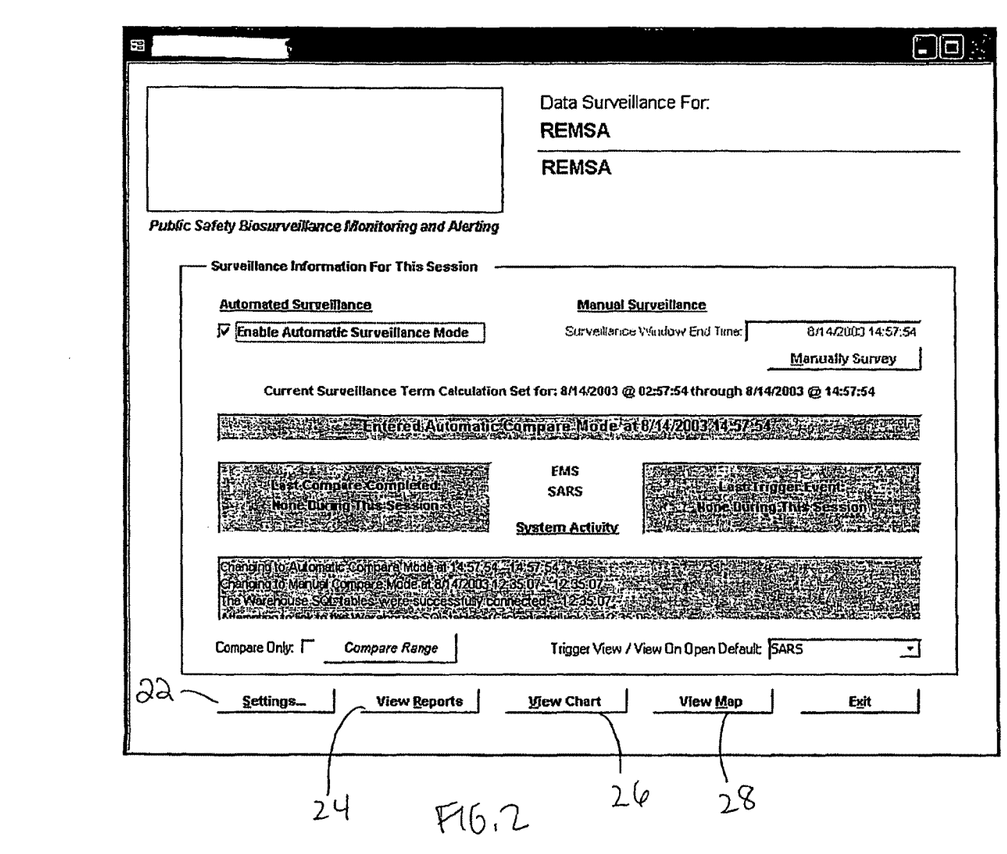
FIG. 2 illustrates a screen capture of the software operating the bio-surveillance system of the present invention showing various selection buttons.

FIG. 2 illustrates a screen capture of the main screen of the software that operates the bio-surveillance system 10 of the present invention. Through this screen, the administrator at the local central computer 18a can set or change the triggers, view the selection of triggers, view a map of the geographical location of the symptoms, or view a report of the reported symptoms.

Figure 8:
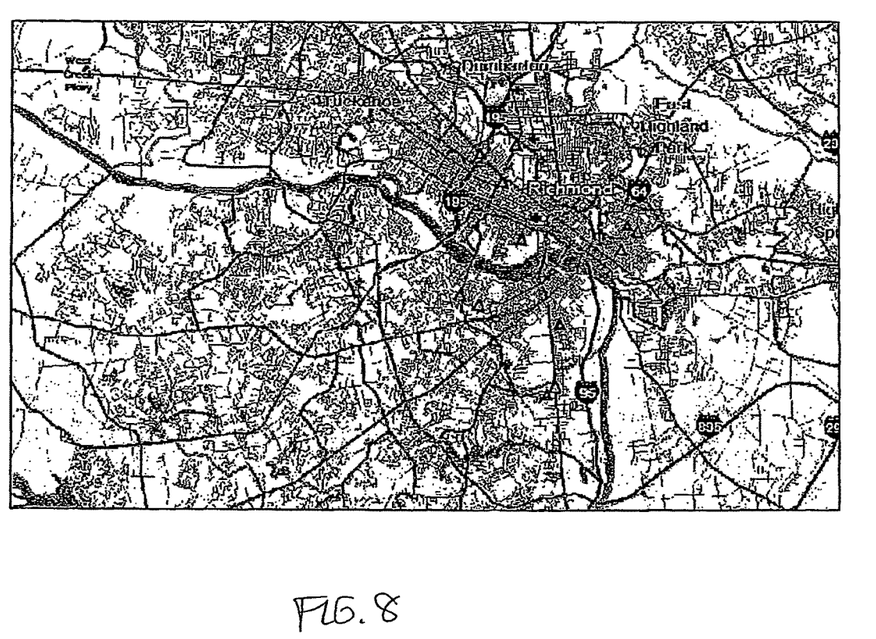
FIG. 8 illustrates a map showing the geographical locations of various symptoms.

For example, if the administrator selects the "settings" button 22, the administrator can modify the triggers. By selecting the "view reports" button 24, the administrator can view various reports related to the reported symptoms, such as a listing of all symptoms and locations (FIG. 10). By selecting the "view chart" button 26, the administrator can view a chart comparing the reported symptoms, the historical data, and the trigger (FIG. 8). By selecting the "view map" button 28, the administrator can view a map of the geographical location showing where the symptoms have been reported (FIG. 9). For example, as shown in FIG. 9, the monitored symptoms appear as triangles. By viewing a map of the symptoms, an administrator can visually see where the symptoms have been reported.

Figure 3:
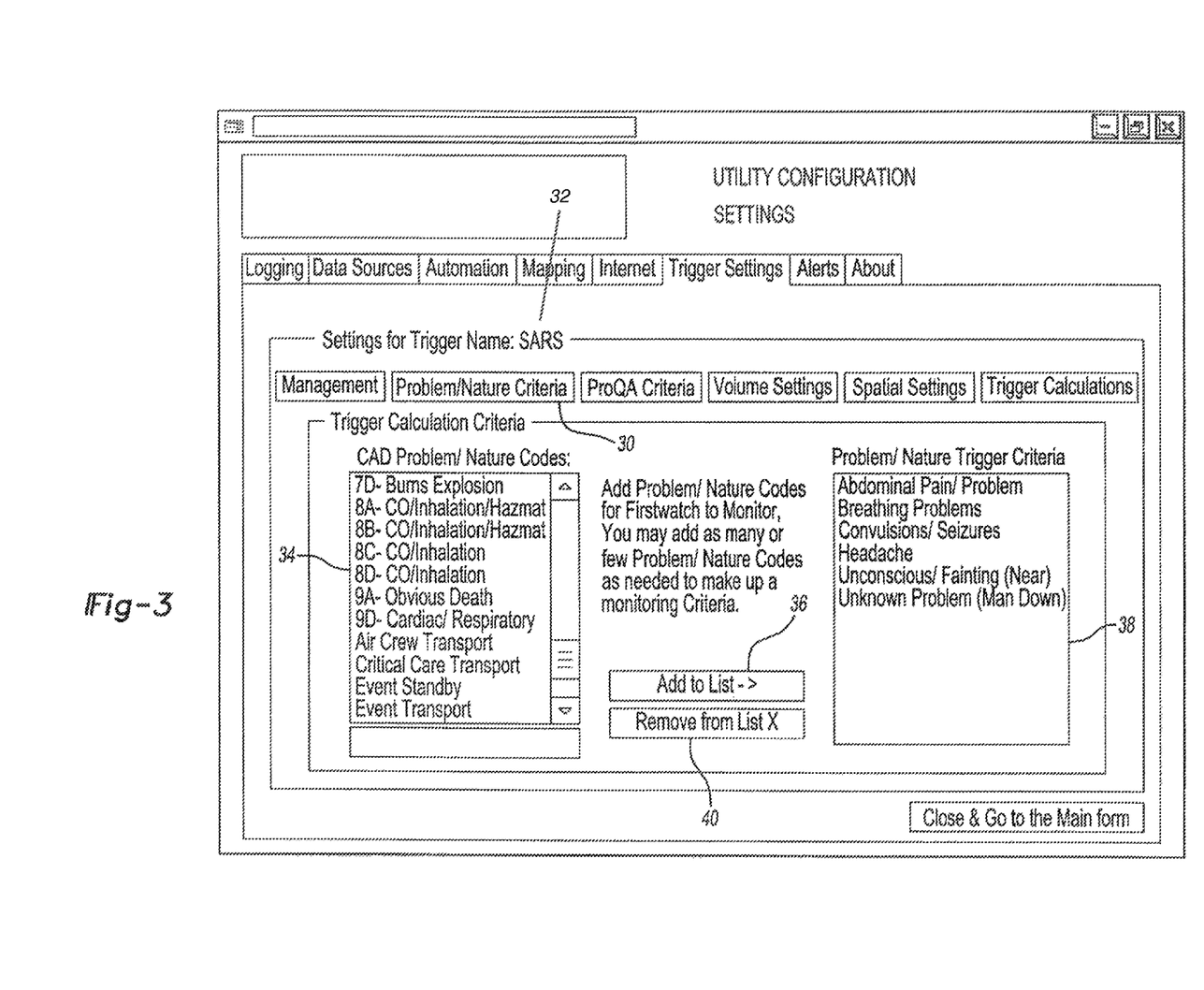
FIG. 3 illustrates a screen capture showing the selection of trigger criteria for a given trigger.

When the administrator wants to change a given trigger, the administrator selects the "settings" button 22, which opens the screen shown in FIG. 3. If the administrator wants to change the symptoms selected for a given trigger, the administrator selects the "problem/nature criteria" tab 30 as shown in FIG. 3, which illustrates an example of a screen capture showing the selection of the symptoms for a given trigger. The name of the trigger that is being modified is inputted into a name field 32. All possible symptoms are listed in a "problem/nature criteria" list 34, which includes a list of all potential symptoms.

When setting a trigger, the administrator can add and remove symptoms by using this screen. For example, when the administrator wants to add a symptom to a trigger, the administrator highlights the symptom in the "problem/nature criteria" list 34 and clicks on the "add to list" button 36. When selected, the symptom appears in a "problem/nature trigger criteria" list 38 which includes a list of all selected symptoms, indicating that the selected symptom is now added to the trigger. A symptom can be removed by selecting and highlighting the symptom in the "problem/nature trigger criteria" list 38 and clicking the "remove from list" button 40 to remove the symptom from the "problem/nature trigger criteria" list 38.

Figure 4:
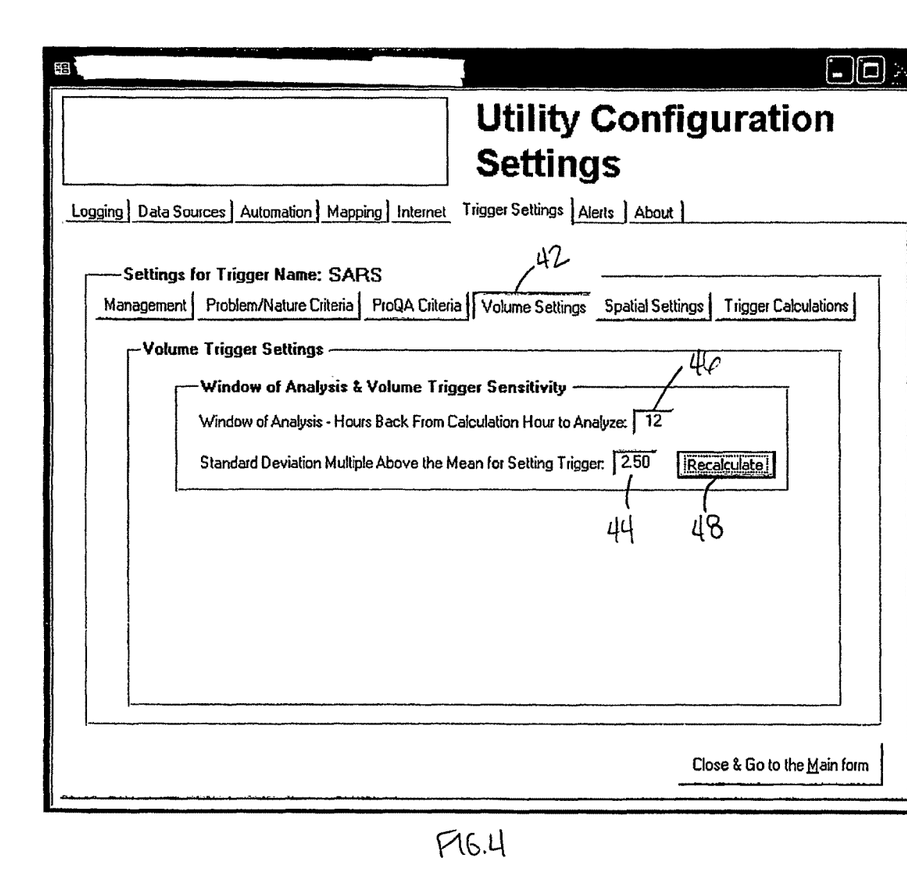
FIG. 4 illustrates a screen capture showing the volume settings of a given trigger.

When the administrator wants to modify the sensitivity of the trigger, the administrator selects the "volume settings" tab 42. The resulting screen is illustrated in FIG. 4. After selecting the "volume settings" tab 42, the administrator can input into the standard deviation field 44 the number of standard deviations of the trigger from the historical average. For example, in response to a threat, the administrator can make a given trigger more sensitive by reducing the trigger from the historical average plus three standard deviations to the historical average plus two standard deviations. The window of analysis, or the amount of time in the past that is analyzed, is inputted into field 46. The number inputted into field 46 determines how far back data is considered to calculate the trigger. In the example shown in FIG. 4, 12-hour trailing data would be the basis of comparison. When the changes are made, the administrator selects the "recalculate" button 48 to recalculate the trigger.

Figure 5:
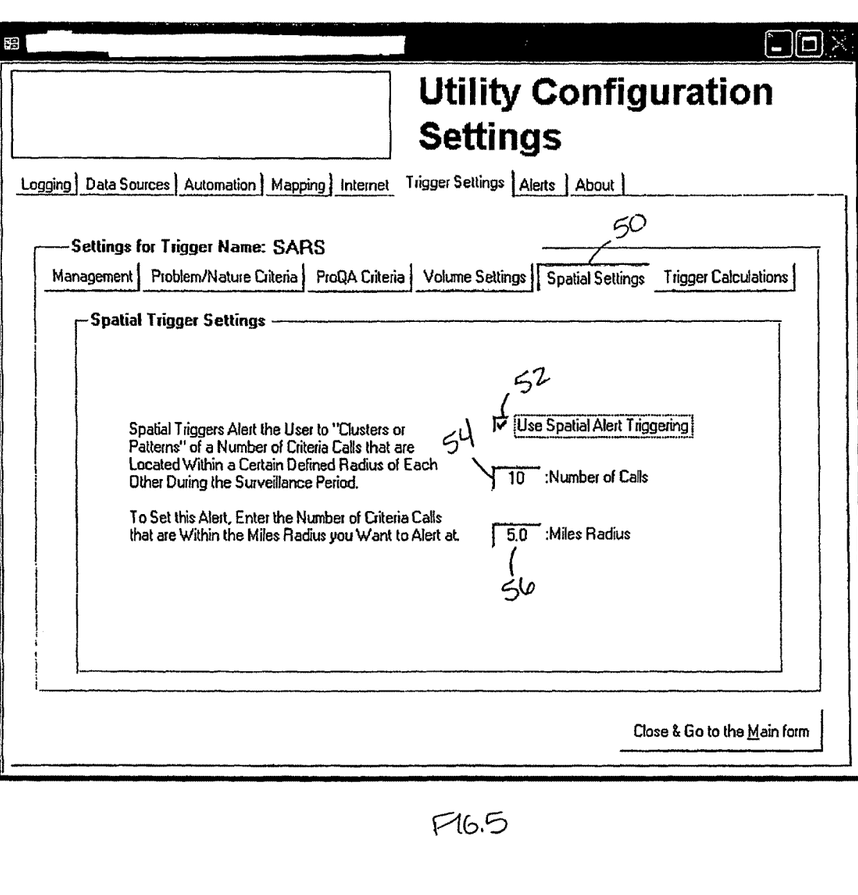
FIG. 5 illustrates a screen capture showing the spatial-spatial settings of a given trigger.

The administrator can also modify a given trigger so that the bio-surveillance system 10 generates an alert if a predetermined number of calls relating to the symptoms in a given trigger are reported in predetermined area by selecting the "spatial settings" tab 50. As shown in FIG. 5, spatial alert triggering is activated by checking the "use spatial alert triggering" box 52. The required number of calls is inputted into the "number of calls" field 54, and the radius of the calls is inputted into the "miles radius" field 56. For example, as shown in FIG. 5, if there are more than 10 calls relating to the symptoms in the selected trigger in a 5 mile radius within 12 hours (from FIG. 4), an alert is generated.

Figure 6:
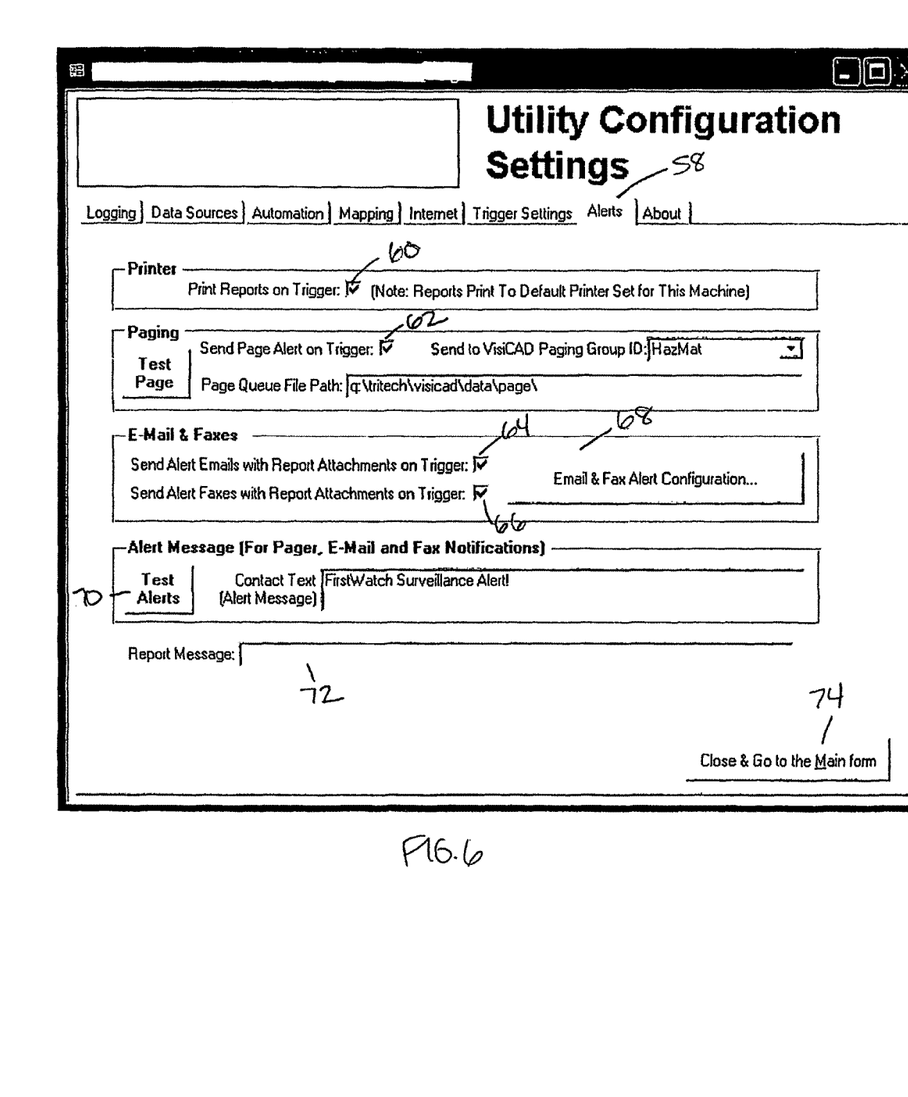
FIG. 6 illustrates a screen capture showing the selection of the manner of generating an alert.

The administrator can select the method of delivering an alert by selecting the "alerts" tab 58. As shown in FIG. 6, the alert can be generated by a printer by selecting the "print reports on trigger" box 60. The alert can be sent to a pager by selecting the "send page alert on trigger" box 62. The alert can be emailed by selecting the "send alert emails with report attachments on trigger" box 64 or faxed by selecting the "send alert faxes with report attachments on trigger" box 66. If the alert is emailed or faxed, the chart showing the reported symptoms and the trigger (FIG. 8), the map of reports (FIG. 9), and the report of the symptoms (FIG. 10) are also sent with the alert. The administrator selects the "email and fax alert configuration" button 68 to program the email addresses and fax numbers that receive the alert. The administrator can test the bio-surveillance system 10 by selecting the "test alerts" button 70 to determine if the system 10 is working properly. The administrator can also program a message to be sent with the alerts in the "report message" field 72. When the administrator is finished modifying the alert from this screen or modifying any of the triggers employing the above-described screens, the administrator selects the "close & go to the main menu" button 74.

Figure 7:
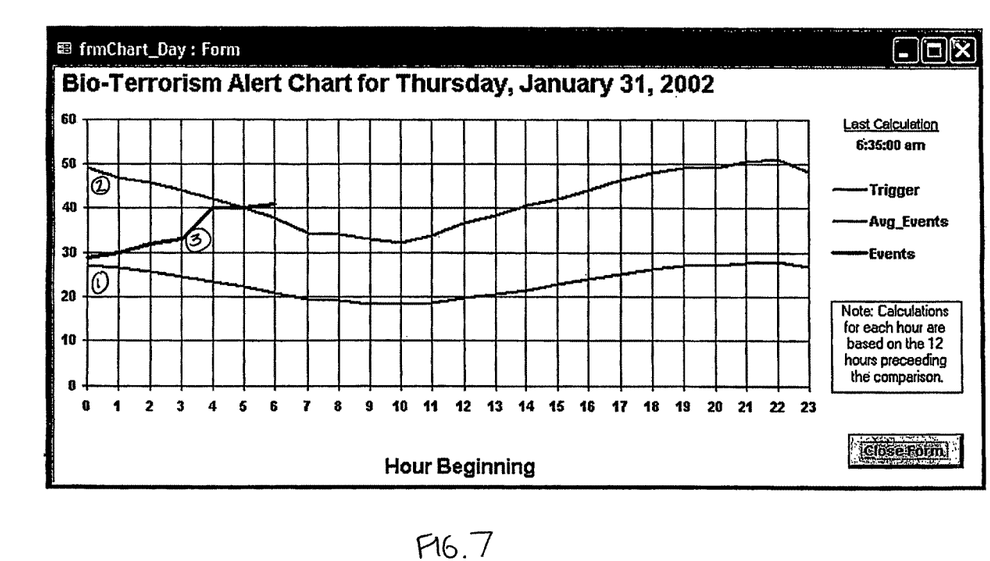
FIG. 7 illustrates a graph illustrating a triggering event, a current event, and a historical event of a trigger on a given day.

FIG. 7 illustrates a graph which displays the monitored symptoms of a given trigger. Line 1 illustrates a line representing the 12-hour trailing average for the symptoms in the trigger during a given day based on historical data. Line 2 illustrates a line representing the trigger. Line 3 illustrates a line representing the actual calls received relating to the symptoms. As shown, at hour 5, the number of calls relating to the symptoms in the trigger exceeds the trigger threshold. Therefore, an alert is generated at hour 5 indicating the possibility of a threat. As described above, the graph can be viewed by selecting the "view map" button 28 of FIG. 2. The map can also be faxed or emailed to a desired person when an alert is generated.

As shown in FIG. 8, the bio-surveillance system 10 also displays occurrences of the symptoms or groups of symptoms on a map for easier evaluation by a human. For example, the location of the selected symptoms or groups of symptoms can be displayed as dots on a street map in a selected geographic area. If the alert is triggered, a user can look at a map for clustering and can begin researching the triggering event. In the screen capture illustrated, the reported symptoms are illustrated as triangles. As described above, the map can be viewed by selecting the "view map" button 28 in FIG. 2. The map can also be faxed or emailed to a desired person when an alert is generated.

FIG. 9 illustrates a report summarizing all of the reported symptoms, the addresses of the calls, and the date and time of the calls inputted into the bio-surveillance system 10. As described above, the report can be viewed by selecting the "view reports" button 24 in FIG. 2. The report can also be faxed or emailed to a desired person when an alert is generated.

The symptoms inputted into the dispatcher computer system 16 can also be monitored remotely. As shown in FIG. 10, the data from the local central computer 18*a* in a geographic area, such as a city, county or state, is sent via a secure encrypted Internet connection to a main central computer 20 which performs the analysis described above on a regional scale. Other local central computers 18*b* and 18*c* from other geographic area also communicate with the main central computer 20.

The main central computer 20 aggregates the data from the multiple local central computers 18*a*, 18*b* and 18*c* for analysis on a local, or and national scale. Even though the main central computer 20 aggregates the data and includes its own triggers, the local central computers 18*a*, 18*b* and 18*c* can each still include their own sets of triggers as described above. However, the main central computer 20 can have different triggers to monitor different types of threats (e.g. more slowly developing threats) because they are monitoring more data from a larger geographic area. Again, these triggers can be changed on the fly based upon the current threat level.

The main central computer 20 can monitor the website of the Office of Homeland Security. If the current threat level changes, the main central computer 20 can adjust the triggers automatically to be more sensitive. For example, if the threat level changes from yellow to orange, the threat level increases. The main central computer 20 can then adjust the triggers in response to this increase to be more sensitive. For example, the trigger can be adjusted from the historical average plus three standard deviations to the historical average plus two standard deviations.

In the bio-surveillance system 10 of the present invention, the triggers are calculated "on the fly." The administrator can define and change a trigger to include certain criteria. For example, the administrator can add a symptom or change the statistical relationship to the historical data based upon the perceived threat and/or vulnerability.

If a threat is received, the administrator can easily increase the sensitivity of the bio-surveillance system 10 by changing the trigger criteria (FIGS. 4 and 5) without taking the system off-line and waiting for the system 10 to rebuild all of the triggers. For example, the sensitivity of the bio-surveillance system 10 can be increased by decreasing the standard deviation field 44 in FIG. 4 from three standard deviations to two standard deviations, so that the trigger changes from the historical average plus three standard deviations to the historical average plus two standard deviations, making the bio-surveillance system 10 more sensitive. The method for implementing the change is described below.

Referring to FIG. 7, the trigger has a historical window, a repeat frequency and period, and an update frequency and period. For example, if the historical window is one year, then the trigger is calculated only based upon data from the preceding year. If the trigger's update frequency is five minutes, then the trigger is updated every five minutes. During an update, the immediately preceding update period (e.g. the immediately preceding five minutes) is added to the historical data while the update period now preceding the historical window (e.g. the five minutes immediately preceding the immediately preceding year) is dropped from the historical data and the trigger is updated based upon the specified statistical criteria. The trigger potentially has distinct values for every update period during its repeat period. For example, the trigger's repeat period may be one week, so that at a given moment, the trigger would have distinct values for each five minute period Sunday through Saturday. Because the update involves only adding five minutes worth of data to the historical data and subtracting five minutes worth of data from the historical data, without recalculating all the data in between, the update can be calculated very quickly.

In the present invention, the criteria for each trigger (FIGS. 4 and 5) can also be changed "on the fly," i.e. without taking the system off-line. If a trigger is changed because of a threat (either a "volume" trigger (FIG. 4), or a "spatial" trigger (FIG. 5)), the trigger must be recalculated. During the time that the new trigger is being recalculated (the "recalculation time"), the bio-surveillance system 10 continues to compare the reported number of the given symptoms to the old trigger. Once the new trigger is calculated after the recalculation time, the new trigger is compared to the reported symptoms. If (as expected) the recalculation time is longer than the normal update period, the next update to the trigger must add the actual data accumulated during the recalculation time to the historical data (while subtracting out a corresponding period from before the historical window). This first update may even take longer than the normal update period, so again the second update would need to include the actual data accumulated during the first update period. This could continue iteratively, with each calculation time being less than the previous until reaching the normal update period.

Alternatively, if the processing power is sufficient relative to the size of the historical data, each trigger could be completely calculated before each comparison of the inputted data to the trigger. Therefore, altering the criteria is no different from updating the trigger.

The frequency of the comparison of the trigger and the inputted data is also variable and can be programmed by the administrator. For example, the inputted data and the trigger can be compared every 5 minutes. Continuing with the above-example, although the trigger is calculated every hour, the local dispatch centers 14a, 14b and 14c send the symptom information to the local central computer 18a after every call or even during each call as the symptoms are entered into the dispatcher computer system 16 for comparison with the trigger.

Although a preferred embodiment is described above, many variations are possible, especially in the statistical analysis of the data. Some examples are described below.

Each symptom in a given trigger can also be provided with a weighting factor. For each symptom having a weighting factor in a given trigger, the number of occurrences of each symptom is multiplied by its weighting factor. The total number of weighted occurrences of all of the symptoms is then compared to the trigger. Each trigger can also require that a specific number of reports of each of the symptoms be required. An alert is activated when the total number of weighted occurrences of the symptoms in the trigger meets or exceeds the trigger.

For example, trigger A can be set at 500 based on the symptoms headache and nausea. When a combined total of 500 reports of weighted headache and weighted nausea are inputted by the emergency services dispatcher in a given geographical area at a given time, an alert is activated. For example, headache has a weighting factor of 3, and nausea has a weighting factor of 2. If 150 reports of headache (150 reports multiplied by the weighting factor of 3) and 75 reports of nausea (75 reports multiplied by the weighting factor of 2) are reported, the weighted total would be 600 and an alert would be triggered as the weighted total exceeds 500.

Alternatively, trigger A can be set to also require a specific number of reports of each of the symptoms. For example, the trigger A can also require in addition to the combined weighted total of 500 reports that 100 reports of headache and 100 reports of nausea be reported. In the described example, only 75 reports of nausea are reported. Therefore, although the weighted total of 500 was exceeded, the individual requirement of 100 reports of nausea was not reached. Therefore, an alert would not be generated. Although these examples have been described, it is to be understood that the parameters for the triggers can vary.

Different symptoms in a specific trigger can have different weighting factors. A symptom can also belong to multiple triggers and can have a different weighting factor in each trigger. For example, in trigger A, headache can have a weighting factor of 2 and nausea can have a weighting factor of 3. In trigger B, headache can have a weighting factor of 3 and nausea can have a weighting factor of 2.

Each trigger can also have its own treatment of the geographic relationship of the symptoms. For example, the trigger can be weighted and include a value which depends on the proximity or clustering of the symptoms. In general, the greater the concentration of the monitored symptoms in a trigger, the more likely the trigger is to be triggered to generate an alert. Alternately, data indicating no grouping or clustering of symptoms will tend to decrease the level of concern. Different statistical or numerical methods can be used to assign a value to the clustering or grouping of the symptoms.

Alternatively, the geographical information is not part of the trigger, but is considered prior to generating an alert. If a trigger is exceeded, the local central computer 18a checks the geographic locations of the symptoms prior to generating an alert. If the central computer 18a determines that the calls are clustered, an alert would be activated. However, if the central computer 18a determines that there is no pattern to the calls, the alert would not be activated.

The triggers can also monitor the rates of change of certain symptoms or groups of symptoms. Depending upon the particular threat monitored by a given trigger, the rate of change of certain symptoms can be important in analyzing the potential occurrence of a threat. Some potential attacks may occur more quickly or more slowly than others. A trigger can be set to consider the rate of change of the symptoms in a given time period. For example, a trigger can be set to monitor the rates of change of certain symptoms or groups of symptoms in a 12-hour trailing period or a 24-hour trailing period. As described above, the trailing period is set by inputting the desired amount of time into the box 46 of FIG. 4.

Filters can also be employed to include or exclude calls based on criteria set in the database. For example, if the temperature in the geographical area increases, a filter can be employed to reduce the weighting of heat related symptoms.

Counter values can also be used in the calculations of the triggers. For example, information about the number of patients transported, the units cancelled prior to arriving on the scene, and the calls waiting in the queue can be detected and used to adjust the trigger. Information from other sources can also be utilized. For example, symptoms experienced by animals reported by veterinarians or animal control centers and symptoms experienced by people in an emergency room can also be inputted into the bio-surveillance system 10.

Although the present invention has been described for use in monitoring potential terrorist threats, this invention is also useful for monitoring other hazards, threats or situations. For example, the present invention is useful for monitoring heat-related emergency dispatch calls, occurrences of food poisoning, rises in levels of gang violence and any other situation that may cause a rise in the number of calls for emergency assistance.

The foregoing description is only exemplary of the principles of the invention. Many modifications and variations of the present invention are possible in light of the above teachings. The preferred embodiments of this invention have been disclosed, however, so that one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

The invention claimed is:

1. A method of activating an alert upon an occurrence of one of a plurality of events and generating and updating a trigger, the method comprising the steps of:
generating a plurality of triggers based upon historical occurrences of at least one health symptom experienced by a plurality of patients, wherein the step of generating is performed by a main computer;
selecting a trigger from the plurality of triggers;
monitoring occurrences of the at least one health symptom within a time window;
comparing the occurrences of the at least one health symptom within the time window to the trigger, wherein the step of comparing the occurrences of the at least one health symptom is performed by the main computer;
activating an alert indicating an occurrence of an event when the occurrences of the at least one health symptom exceed the trigger;
updating the trigger at an update frequency, wherein the step of updating the trigger includes adding new occurrences to the historical occurrences and dropping old occurrences from the historical occurrences, the step of updating the trigger is performed by the main computer, the trigger is based upon criteria, and the criteria changes based on a date and a time and depends on the date and the time; and
changing the criteria used to determine the trigger and then recalculating the trigger based upon the changed criteria:
wherein the step of monitoring occurrences of the at least one health symptom within a time window comprises:
receiving, from a computing device of an emergency service dispatcher, data describing occurrences of the at least one health symptom within a time window and data describing, for each occurrence, a respective geographical location from which the occurrence was reported to the emergency services dispatcher; and
determining a geographic location of each of the occurrences of the at least one health symptom based on the data that describes the respective geographical locations, and associating the determined geographical locations with each of the at least one health symptom;
wherein the step of activating an alert indicating an occurrence of an event when the occurrences of the at least one health symptom exceed the trigger comprises:
determining whether one of the plurality of events has occurred based on the comparing, and further based on a proximity of the determined geographical locations; and
if the determining indicates that one of the events has occurred, activating the alert;
the method further comprising selectively excluding data from a given emergency services dispatcher call from the determination of weather one of the plurality of events has occurred based on a temperature of the geographical area from which the call originates.

2. The method as recited in claim 1 further including the step of receiving the occurrences of the at least one health symptom from an emergency services dispatcher, and the occurrences of the at least one health symptom entirely include information collected by the emergency services dispatcher.

3. The method as recited in claim 2 wherein the respective geographical locations are located in a first geographical area.

4. The method as recited in claim 3 further including the step of accumulating occurrences of the at least one health symptom in a second geographical area which includes the first geographical area and which is larger than the first geographical area.

5. The method as recited in claim 3 wherein information about the at least one health symptom is provided at a variable time.

6. The method as recited in claim 1 further including the steps of receiving a geographic location of each of the occurrences of the at least one health symptom and associating the geographical location with each of the occurrences of the at least one health symptom.

7. The method as recited in claim 6 further including the step of displaying the geographical location of each of the occurrences of the at least one health symptom on a display.

8. The method as recited in claim 1 further including the step of adjusting a first trigger to generate a new trigger and then comparing the new trigger to the occurrences.

9. The method as recited in claim 1 wherein the trigger is a statistical variation of historical values of the occurrences of the at least one health symptom.

10. The method as recited in claim 1 further including the step of weighting the at least one health symptom relative to one another.

11. The method as recited in claim 1 further including the step of calculating the trigger prior to the step of comparing the occurrences of the at least one health symptom to the trigger.

12. The method as recited in claim 1 wherein the at least one health symptom includes headache, fever, fainting, clammy, unconscious, bleeding, vomiting and nausea.

13. The method as recited in claim 1 wherein the plurality of events includes at least one of a biological attack and a chemical attack.

14. The method as recited in claim 1 wherein the at least one health symptom includes a plurality of symptoms, and the criteria for the trigger includes the plurality of symptoms, the step of changing the criteria including the step of adding a symptom to or deleting a symptom from the at least one health symptom.

15. The method as recited in claim 1 wherein the criteria for the trigger includes the plurality of symptoms and a statistical relationship to the historical occurrences, and the step of changing the criteria includes the step of changing the statistical relationship to the historical occurrences.

16. The method of claim 1 further including the step of adjusting a sensitivity of the trigger.

17. The method of claim 16 wherein the step of adjusting the sensitivity of the trigger is based on a national threat level.

18. The method of claim 1 further including the steps of contacting an emergency services dispatcher to report the at least one health symptom and then inputting the at least one health symptom into a dispatcher computer.

19. The method of claim 1 wherein the occurrences of the at least one symptom are collected from information obtained from phone calls to an emergency services dispatcher.

20. The method of claim 19 wherein the alert is activated when there is a predetermined number of the phone calls relating to the at least one symptom within a radius of a location.

21. The method of claim 1, wherein the determining of whether one of the plurality of events has occurred is further based on a rate of change of how frequently the symptoms are occurring.

* * * * *

UNITED STATES PATENT AND TRADEMARK OFFICE
CERTIFICATE OF CORRECTION

PATENT NO. : 9,642,562 B2
APPLICATION NO. : 10/524918
DATED : May 9, 2017
INVENTOR(S) : Todd Stout Page 1 of 1

It is certified that error appears in the above-identified patent and that said Letters Patent is hereby corrected as shown below:

In the Claims

In Claim 1, Column 10, Line 12; after "determination of" replace "weather" with --whether--

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*